(12) United States Patent
Swanson et al.

(10) Patent No.: US 8,486,461 B2
(45) Date of Patent: *Jul. 16, 2013

(54) METHODS FOR IMPROVING THE APPEARANCE OF AGING SKIN USING A COMPOSITION COMPRISING BANYAN TREE, LOTUS, AND CLOVER SERUM FRACTIONS

(75) Inventors: Cheri Lynn Swanson, West Chester, OH (US); Leo Timothy Laughlin, II, Mason, OH (US); Deborah Ruth Finlay, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,677

(22) Filed: Feb. 22, 2012

(65) Prior Publication Data

US 2012/0237460 A1    Sep. 20, 2012

Related U.S. Application Data

(60) Provisional application No. 61/445,494, filed on Feb. 22, 2011.

(51) Int. Cl.
*A61K 36/00* (2006.01)
*A61K 8/00* (2006.01)

(52) U.S. Cl.
USPC .......................................... 424/725; 424/401

(58) Field of Classification Search
USPC .................................. 424/401, 725
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 5,925,348 A * | 7/1999 | Riley et al. | 424/94.5 |
| 6,468,564 B1 | 10/2002 | Riley | |
| 6,485,756 B1 * | 11/2002 | Aust et al. | 424/725 |
| 7,442,391 B2 * | 10/2008 | Koganov | 424/725 |
| 8,277,852 B2 * | 10/2012 | Koganov et al. | 424/725 |
| 2004/0175347 A1 | 9/2004 | Bissett | |
| 2005/0158396 A1 * | 7/2005 | Kraechter et al. | 424/490 |
| 2006/0275237 A1 | 12/2006 | Bissett | |
| 2008/0206373 A1 | 8/2008 | Millikin | |
| 2011/0212190 A1 * | 9/2011 | Koganov et al. | 424/711 |
| 2012/0201768 A1 * | 8/2012 | Swanson et al. | 424/62 |
| 2012/0237459 A1 | 9/2012 | Swanson | |
| 2012/0237460 A1 | 9/2012 | Swanson | |

FOREIGN PATENT DOCUMENTS

| | | |
|---|---|---|
| DE | 10329004 | 1/2005 |
| EP | 1344516 A1 | 9/2003 |
| JP | 2003048846 A * | 2/2003 |
| JP | 2008184416 A * | 8/2008 |
| WO | 02087533 A1 | 11/2002 |
| WO | 2005041996 A1 | 5/2005 |

OTHER PUBLICATIONS

Miyahira, M., JP 2008-184416A, Aug. 14, 2008, machine translation.*
Honda, H. et al., JP 2003-048846 A, Feb. 21, 2003, machine translation.*
Poudher's Perfumes, Cosmetics and Soaps, 2000, Kluwer Academinc Publishers, (10th ed. by Hilda Butler), p. 411.*
Kovali, Michael. Claudins—"Key Pieces in the Tight Junction Puzzle. Cell Communication and Adhesion" 13:127-138, 2006.
Chikuma M"Aquaporin-3 functions as a glycerol transporter in mammalian skin," Hara-, Biol Cell. Jul. 2005;97(7):479-86.
Hara, "Glycerol replacement corrects defective skin hydration, elasticity, and barrier function in aqaporin-3-deficient mice,", Proc Natl Acad Sci U S A. Jun. 10, 2003;100(12):7360-5. Epub May 27, 2003.
International Search Report; International Application No. PCT/US2012/026139; date of mailing Sep. 20, 2012; 13 pages.
U.S. Appl. No. 13/402,608, filed Feb. 22, 2012, Cheri Lynn Swanson, et al.

* cited by examiner

*Primary Examiner* — Gina C Justice
(74) *Attorney, Agent, or Firm* — John G. Powell; Melody A. Jones

(57) ABSTRACT

A method of improving the appearance of aging skin may comprise the step of applying a composition comprising an effective amount of banyan tree serum fraction, lotus serum fraction, and clover serum fraction to a sign of aging on a skin surface, wherein the composition is applied for a period of time sufficient to improve the appearance of the aging skin. The method may include the step of identifying a sign of aging on a facial skin surface.

20 Claims, 1 Drawing Sheet

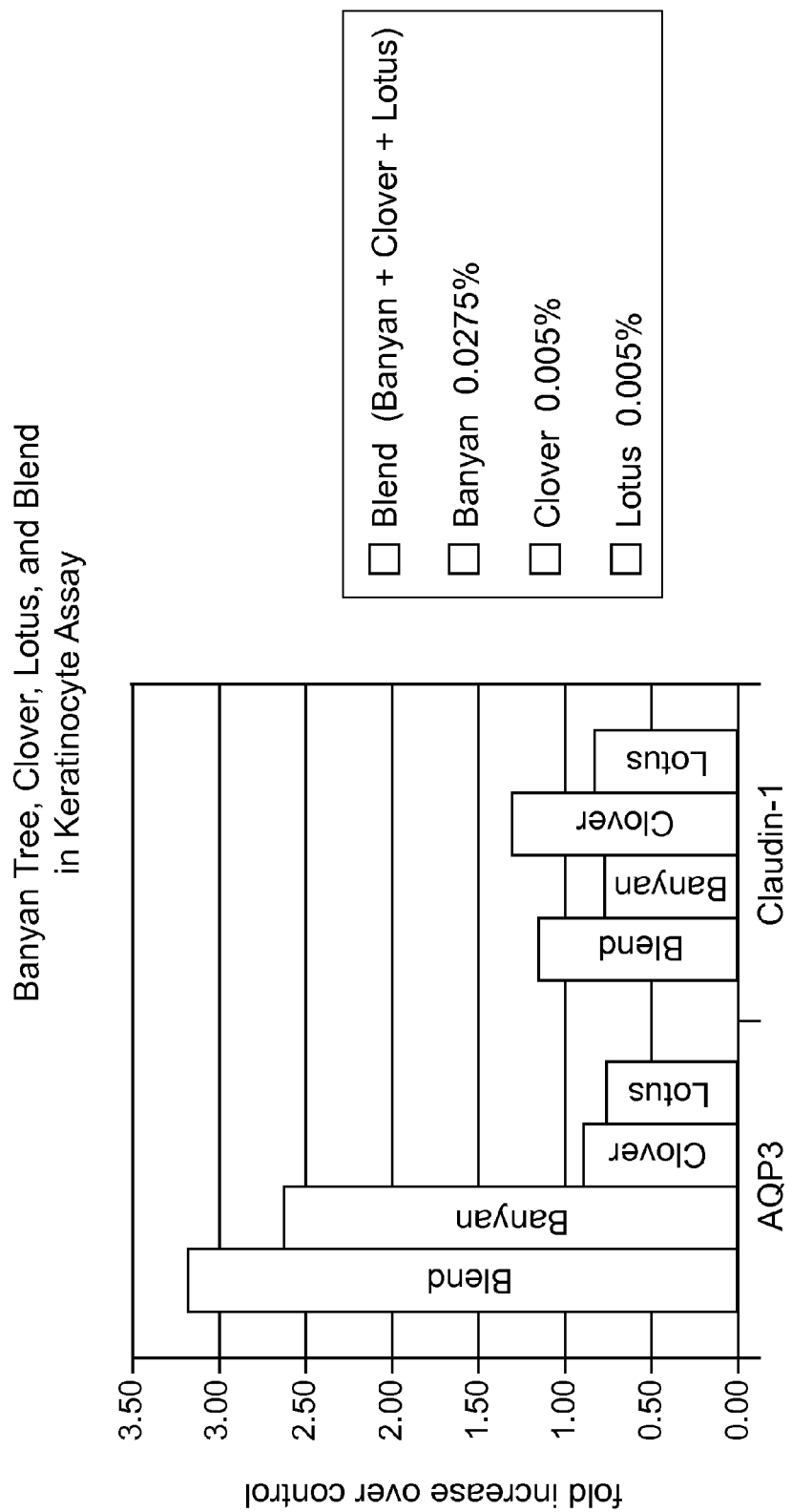

METHODS FOR IMPROVING THE APPEARANCE OF AGING SKIN USING A COMPOSITION COMPRISING BANYAN TREE, LOTUS, AND CLOVER SERUM FRACTIONS

CROSS REFERENCE TO RELATED APPLICATION

This application claims the benefit of U.S. Provisional Application No. 61/445,494, filed Feb. 22, 2011.

FIELD OF THE INVENTION

The present invention relates to methods for improving the appearance of aging mammalian skin using a composition comprising banyan tree, lotus, and clover serum fractions.

BACKGROUND OF THE INVENTION

The epidermis, the outermost layer of the skin, comprises a cellular continuum of four layers: the stratum corneum, the granular layer, the spinous layer, and the basal layer. Each cellular layer in the epidermis represents various stages along a process in which basal epidermal keratinocytes undergo a continuous cycle of proliferation, differentiation, and apoptosis, moving upward from the basal layer to finally yield corneocytes. These corneocytes form the cornified layer known as the stratum corneum.

Basal keratinocytes reside at the lower portion of the epidermis. These mitotically active cells undergo a proliferative cycle to generate daughter cells that are physically dislocated upward into the spinous and granular layers and undergo the process of differentiation into corneocytes. On passing through the spinous and granular layers, the cells undergo morphological changes that render them flatter in structure as they lose their cellular viability, undergo alternate keratin expression profiles, and transform into cellular remnants. On average, a younger-aged epidermis turns over in about one month, shedding the older cells and replacing them with newer ones, but this process can increase to over forty days in older skin.

The stratum corneum's corneocytes remain connected to one other via proteins and lipids, creating a protective barrier between the organism and its outside environment. This tightly regulated epidermal permeability barrier functions as a physical and selective barrier against chemical and biological insults Important functions of this barrier include attenuation of the penetration of free radicals and prevention of penetration of harmful radiation, including UV radiation, into deeper layers. The stratum corneum also acts as a permeability barrier and functions to prevent loss of body moisture to the outside environment. Dysfunction of this barrier can lead to chronic skin conditions, diseases, and in extreme cases can even threaten the viability of the organism.

Skin aging is a multifactorial process driven by both intrinsic (chronological aging) and extrinsic (environmental) factors, including ultraviolet (UV) exposure, environmental toxins, pollutants, and smoking. It is well known in the art that the ability of the stratum corneum to cyclically generate new layers of skin diminishes with age so that the stratum corneum turnover rate is substantially reduced in aged skin, with the cornified layer becoming gradually thinner. This results in a reduction in the functioning capacity of the barrier so that harmful stimuli penetrate the stratum corneum more easily, leading to UV-damage, for example, of the underlying dermal layers, degradation of collagen and elastin, and eventually manifests in appearance as wrinkling and skin atrophy. Thinning of the stratum corneum by the sum of intrinsic and extrinsic aging factors increases the visible appearance of fine lines and wrinkles Further, the barrier suffers from an age-related increase in permeability to free radicals and a reduction in the amount of lipid in the intercellular matrix, decreasing barrier capacity to diffuse toxins from deeper layers. Recovery capacity of the barrier to environmental insult is also substantially reduced with age.

Thus, the skin's barrier function is key to the skin's ability to regenerate and protect itself from the appearance of aging skin. Accordingly, it would be desirable to provide compositions and methods of treatment that can improve the skin's barrier function and also improve the appearance of aging skin.

SUMMARY OF THE INVENTION

A method of improving the appearance of aging skin comprising the step of applying a first composition comprising an effective amount of banyan tree serum fraction, lotus serum fraction, and clover serum fraction blend to an area of aging skin, wherein the composition is applied for a period of time sufficient to improve the appearance of the aging skin. In certain embodiments the composition also comprises a dermatologically acceptable carrier.

In some embodiments the area of aging skin is aging facial skin In particular embodiments, improving the appearance of aging skin comprises improving the appearance of wrinkles, fine lines, coarse deep lines, crevices, bumps, large pores; thickening of keratinous tissue (e.g., building the epidermis and/or dermis and/or sub-dermal layers of the skin); increasing the convolution of the dermal-epidermal border (also known as the rete ridges); skin lightening; preventing loss of skin elasticity, for example, due to loss, damage and/or inactivation of functional skin elastin, resulting in such conditions as elastosis, sagging, loss of skin recoil from deformation; change in coloration to the skin, for example, under-eye circles, blotchiness (e.g., uneven red coloration due to, for example, rosacea), sallowness, discoloration caused by hyperpigmentation, etc.; and combinations thereof.

In response to the problems identified in the background, the present invention may take other forms. Further forms of the present invention will be appreciated in the detailed description that follows.

BRIEF DESCRIPTION OF THE DRAWINGS

It is believed that the present invention will be better understood from the following description taken in conjunction with the accompanying drawings. The referenced drawings are not to be construed as limiting the scope of the present invention.

FIG. 1 is a bar graph showing the up-regulation of aquaporin-3 (AQP3) and claudin-1 when banyan tree, clover, and lotus serum fractions are evaluated separately and as a blend in a keratinocyte assay.

DETAILED DESCRIPTION OF THE INVENTION

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a human skin surface such as the epidermis.

The term "dermatologically acceptable" as used herein means that the compositions or components described are suitable for use in contact with human skin tissue without undue toxicity, incompatibility, instability, allergic response, and the like.

The term "effective amount" as used herein means an amount of a compound or composition sufficient to significantly induce a positive appearance and/or feel benefit, but low enough to avoid serious side effects (i.e., to provide a reasonable benefit to risk ratio, within the scope of sound judgment of the skilled artisan). As used herein, "effective amount" in relation to the banyan tree, lotus, and clover blend means an amount of the three materials in combination sufficient to significantly induce a positive appearance and/or feel benefit, but low enough to avoid serious side effects (i.e., to provide a reasonable benefit to risk ratio, within the scope of sound judgment of the skilled artisan).

The term "post-inflammatory hyperpigmentation" as used herein refers to an acute to chronic increase in pigmentation as a response to a transient inflammatory event. Post-inflammatory hyperpigmentation is particularly prevalent in, but not limited to, dark skin subjects. Post-inflammatory hyperpigmentation typically subsides once the transient inflammatory event dissipates. Examples of transient inflammatory events include, but are not limited to, acne lesions, ingrown hairs, scratches, insect bites, surfactant damage, and short-term UV exposure.

The term "hyperpigmented spot" as used herein refers to a defined area of skin wherein the pigmentation is greater than that of an adjacent area of skin due to localized and chronic or systemic overproduction of melanin Hyperpigmented spots typically are between about 2 mm and about 10 mm in diameter but smaller or larger spots are possible. Hyperpigmentation spots can include one or more of age spots, sun spots, solar lentigos, hypo-melanotic lesions, freckles, and melasma spots.

The term "age spots" as used herein refers to aging spots wherein the pigmentation is due to localized and chronic overproduction of melanin caused by intrinsic or extrinsic aging factors.

The term "skin tone agent" as used herein refers to an agent that regulates melanin production signals, synthesis of melanin, systemic transfer of melanin between the melanocyte and the keratinocyte, and/or melanin degradation. Skin tone agents can improve the appearance of uneven skin tone by acting as a lightening or pigmentation reduction cosmetic agent.

The term "skin tone" as used herein refers to the overall appearance of melanin in the skin caused by the systemic, rather than transient, synthesis of melanin. Skin tone is typically characterized over a larger area of the skin. The area ideally may be than 100 $mm^2$, but larger areas are envisioned such as the entirety of the facial skin or any of the facial skin surfaces. Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data.

The term "facial skin surface" as used herein refers to one or more of forehead, periorbital, cheek, perioral, chin, and nose skin surfaces.

"Skin care actives," or "actives," as used herein, means compounds that, when applied to the skin, provide a benefit or improvement to the skin "Improving the appearance of aging skin" means effecting a visually and/or tactilely perceptible positive change, or benefit, in skin appearance and/or feel. As used herein, "improving the appearance of aging skin" also includes preventing or delaying the appearance of aging skin. Benefits that may be provided include, but are not limited to, one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin); increasing the convolution of the dermal-epidermal border (also known as the rete ridges); skin lightening; preventing loss of skin elasticity, for example, due to loss, damage and/or inactivation of functional skin elastin, resulting in such conditions as elastosis, sagging, loss of skin recoil from deformation; change in coloration to the skin, for example, undereye circles, blotchiness (e.g., uneven red coloration due to, for example, rosacea), sallowness, discoloration caused by hyperpigmentation, etc.

"Signs of skin aging," as used herein, include but are not limited to, all outward visibly and tactilely perceptible manifestations, as well as any macro- or microeffects, due to skin aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin "Hyperpigmentation," as used herein, refers to an area of skin wherein the pigmentation is greater than that of an adjacent area of skin (e.g., a pigment spot, an age spot, and the like).

"Desquamation, exfoliation, and/or turnover," as used herein, mean the removal of the upper layers of the stratum corneum (comprising the horny layers).

"Sallowness," as used herein means the pale color, yellow color or the like condition of skin that occurs as a result of a loss of, damage to, alterations to, and/or abnormalities in skin components such that they become colored (e.g., yellow in color) due to processes such as protein glycation and accumulation of lipofuscin or in the decrease in peripheral blood flow that typically accompanies skin aging.

As used herein, "exogenous solvent" means any solvent that is not inherently present in the plant material, but is placed in contact with the plant material for the purpose of separating (e.g., extracting) compounds from the plant material.

I. Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

A. Serum Fractions

Compositions of the present invention comprise effective amounts of banyan tree serum fraction, lotus serum fraction, and clover serum fraction.

Banyan tree, lotus, and clover serum fractions consist essentially of the flower, leaf, and stem serum fractions obtained from *Ficus Benghalensis, Nelumbo Nucifera*, and *Trifolium Pratense*, respectively. Preferred serum fractions herein are produced by Integrated Botanical Technologies, LLC, of Ossining, N.Y., USA, under the trade names Ficus Bengalensis Enriched Serum Fraction™ (INCI Name: *Ficus Indica* Flower/Leaf/Stem Juice), Lotus Enriched Serum Fraction™ (INCI Name: *Nelumbo Nucifera* Flower/Leaf/Stem Juice), and Red Clover Enriched Serum Fraction™ (INCI Name: *Trifolium Pratense* (Clover) Flower/Leaf/Stem Juice).

In some embodiments, the composition may comprise banyan tree serum fraction in an amount of from 0.001% to 15%, alternatively from 0.002% to 10%, alternately from 0.025% to 10%, in other embodiments from 0.05% to 10%, in others from 0.05% to 5%, and in others from 0.1% to 5%, by weight of the total composition. The composition may comprise lotus serum fraction in an amount of from 0.001% to 15%, alternatively from 0.002% to 10%, alternatively from 0.01% to 15%, alternately from 0.025% to 10%, in other embodiments from 0.05% to 10%, in others from 0.05% to 5%, and in others from 0.1% to 5%, by weight of the total composition. The composition may comprise clover serum fraction in an amount of from 0.001% to 15%, alternatively from 0.002% to 10%, alternatively from 0.01% to 15%, alternately from 0.025% to 10%, in other embodiments from 0.05% to 10%, in others from 0.05% to 5%, and in others from 0.1% to 5%, by weight of the total composition.

The method for making a serum fraction comprises the steps of: (a) separating cell juice from clean, fresh, un-wilted plant matter to obtain fresh cell juice, wherein no exogenous liquid is added prior or during said separating; (b) filtering said fresh cell juice to obtain fiber-free cell juice; and (c) fractionating said fiber-free cell juice to obtain the serum fraction for use herein. Suitable serum fraction preparation methods are set forth in U.S. Pat. No. 7,442,391, "Bioactive Botanical Cosmetic Compositions and Processes for their Production," to Koganov, and in co-pending U.S. Provisional Application Ser. No. 61/381,748 (P&G Case 11870P), filed 10 Sep. 2010 by Swanson et al.

The resulting serum fractions have superior bioactivity versus traditionally prepared plant extracts. Unlike traditional extracts, the serum fraction is prepared from fresh plant cell juice that has been mechanically separated from the rest of the fresh plant material. Importantly, no exogenous solvent (e.g., water, hexane, acetone, ethanol) is added during the juice separation process. The resulting cell juice contains the full spectrum of compounds found in fresh plant matter, thus the resulting serum fractions contain a much broader range of active compounds than do traditional plant extracts, which contain only the narrow range of compounds that can be separated with a particular solvent.

Furthermore, using fresh plants maintains the integrity of the bioactive components inherently present in the fresh plant matter. Traditional plant extracts are not prepared from fresh plant matter, but rather from dried plant material, which has undergone degradation due to dehydration. During dehydration, the cell walls are compromised, causing the degradation of compounds through mechanisms such as hydrolysis, oxidation, polymerization, Maillard reactions, and isomerization. When the dried leaves are extracted, the resulting extract thus contains these degradation products that were not originally present in the fresh plant matter. Accordingly, the composition of the resulting dry leaf extract greatly differs from that of fresh juice and the resulting serum fraction.

B. Skin Tone Agent

In some embodiments, it may be desirable to include a skin tone agent in the composition. The skin tone agents can be included to further improve overall skin tone. When present, the compositions of the present invention contain up to about 50%, 40%, 30%, 20%, 10%, 5%, or 3%, by weight of the composition, of the skin tone agent. When present, the compositions of the present invention contain at least about 0.001%, 0.01%, 0.1%, 0.2%, 0.5%, or 1%, by weight of the composition, of the skin tone agent. Suitable ranges include any combination of the lower and upper limits including suitable ranges from about 0.1% to about 50%; from about 0.2% to about 20%; or from about 1% to about 10%, by weight of the composition, of the skin tone agent. The amounts listed herein are only to be used as a guide, as the optimum amount of the skin tone agent will depend on the specific active selected since their potency does vary considerably.

Suitable skin tone agents include, but are not limited to, sugar amines, vitamin B3 compounds, arbutin, deoxyarbutin, 1,3-dihydroxy-4-alkylbenzene such as hexylresorcinol, sucrose dilaurante, bakuchoil (4-[(1E,3S)-3-ethenyl-3,7-dimethyl-1,6 octadienyl]phenol or monterpene phenol), pyrenoine (available from Biotech Marine, France), panicum miliaceum seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, helianthus annuus (sunflower) and vitis vinifera (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename Sepiwhite by Seppic, France), kojic acid, hexamidine compounds, salicylic acid, and retinoids including retinol and retinyl propionate.

In certain embodiments, the additional skin tone agent is selected from vitamin B3 compounds, sugar amines, hexamidine compounds, salicylic acid, 1,3-dihydroxy-4-alkylbenzene such as hexylresorcinol, and retinoids. As used herein, "vitamin $B_3$ compound" means a compound having the formula:

wherein R is —CONH₂ (i.e., niacinamide), —COOH (i.e., nicotinic acid) or —CH₂OH (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "hexaminide compound" means a compound having the formula:

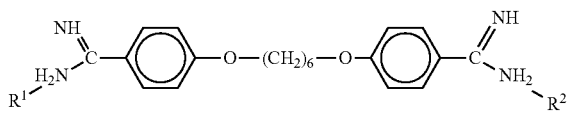

wherein $R^1$ and $R^2$ are optional or are organic acids (e.g., sulfonic acids, etc.). In one embodiment, hexamidine compound is hexamidine diisethionate.

C. Anti-Inflammatory Agents

Hyperpigmentation may result from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions of the present invention an anti-inflammatory agent. When present, the compositions of the present invention contain up to about 20%, 10%, 5%, 3%, or 1% by weight of the composition, of the anti-inflammatory agent. When present, the compositions of the present invention contain at least about 0.001%, 0.01%, 0.1%, 0.2%, 0.3%, 0.5%, or 1%, by weight of the composition, of the anti-inflammatory agent. Suitable ranges include any combination of the lower and upper limits Suitable anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly *Commiphora mukul*), kola extract, chamomile, and sea whip extract (extracts from plant in the order Gorgonacea), derivatives of any of the foregoing, and mixtures thereof.

D. Sunscreen Actives

The compositions of the subject invention may comprise one or more sunscreen actives (or sunscreen agents) and/or ultraviolet light absorbers. Herein, "sunscreen active" collectively includes sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In one embodiment, the composition may comprise from about 1% to about 20%, and alternatively from about 2% to about 10% by weight of the composition, of the sunscreen active. Exact amounts will vary depending upon the chosen sunscreen active and the desired Sun Protection Factor (SPF), which is within the knowledge of one of skilled in the art.

E. Optional Components

The compositions of the present invention may contain a variety of other ingredients provided that they do not unacceptably alter the benefits of the invention. When present, compositions of the present invention may contain from about 0.0001% to about 50%; from about 0.001% to about 20%; or, alternately, from about 0.01% to about 10%, by weight of the composition, of the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

The Personal Care Product Council's *International Cosmetic Ingredient Dictionary and Handbook*, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

F. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the components (e.g., extracts, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and *McCutcheon's Detergents and Emulsifiers*, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

II. Methods of Treatment

Various methods of treatment, application, regulation, or improvement may utilize the aforementioned compositions. Identification of a region of aging skin may occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, identification of the region of aging skin may be on a facial skin surface including the forehead, perioral, chin, periorbital, nose, and/or cheek skin surfaces.

One suitable method of improving the appearance of aging skin includes the step of topically applying a composition comprising an effective amount of banyan tree serum fraction, lotus serum fraction, and clover serum fraction blend to the aging skin surface, wherein the composition is applied for a period of time sufficient for the serum fraction blend to improve the appearance of the aging skin.

The method may comprise the step of applying the composition to the previously identified area of aging skin, or an area where one seeks to prevent the appearance of aging skin. Many regimens exist for the application of the composition. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before bed.

The treatment period is ideally of sufficient time to provide an improvement in the appearance of aging skin. The treatment period may be at least about 1 week, and in some embodiments the treatment period may last about 4 weeks or about 8 weeks. In certain embodiments, the treatment period will extend over multiple months (i.e., 3-12 months) or multiple years. In one embodiment the composition is applied at least once a day during a treatment period of at least about 4 weeks or at least about 8 weeks. In one embodiment the composition is applied twice a day during a treatment period of at least about 4 weeks or 8 weeks.

The step of applying the composition may be accomplished by localized application. In reference to application of the composition, the terms "localized", "local", or "locally" mean that the composition is delivered to the targeted area (such as age spots) while minimizing delivery to skin surface not requiring treatment. The composition may be applied and lightly massaged into area of aging skin. The form of the composition or the dermatologically acceptable carrier should be selected to facilitate localized application. While certain embodiments of the present invention contemplate applying a composition locally to an area, it will be appreciated that compositions of the present invention can be applied more generally or broadly to one or more skin surfaces.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to age spots having an approximate diameter between about 2 mm and about 10 mm and allowing for a dosed amount of the composition of between about 1 to about 50 uL/cm$^2$ or between about 1 to about 5 uL/cm$^2$. In another embodiment, the composition is applied to the one or more aging spots and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required and the compositions of the present invention can also be applied directly by using one's finger or in other conventional manners.

In one embodiment, the method comprises the steps of applying a first composition comprising an effective amount of banyan tree serum fraction, lotus serum fraction, and clover serum fraction to a skin surface and of applying a second composition to the skin surface, before or after the first composition. The first and second compositions may be any compositions described herein; however, the second composition may optionally comprise an effective amount of the serum fractions present in the first composition. The second composition may comprise one or more tone agents, sunscreen actives, anti-inflammatory agents, or optional components. The first composition may be generally or locally applied, while the second composition may be generally or locally applied to the skin surface including the aging skin to which the first composition is applied. In certain embodiments, the skin surface is facial skin surface which includes one or more of the forehead, perioral, chin, periorbital, nose, and cheek skin surfaces. In another embodiment, the first and second compositions are applied contemporaneously to at least the cheek, forehead, and chin/perioral skin surfaces. For general application to a skin surface and, particularly a facial skin surface, the dosed amount of the first or second composition may be between about 1 to about 50 uL/cm² per application (i.e., per single application to the skin surfaces).

Suitable methods may comprise any one or more of the abovementioned steps. All of the aforementioned steps are applicable to application, treatment, regulation, and/or improvement of aging skin appearance.

VI. Mechanisms of Action

The stratum corneum is a tightly regulated epidermal permeability barrier and functions as a physical and selective barrier against chemical and biological insults, as well as acts as a permeability barrier to prevent loss of body moisture to the outside environment. The stratum corneum's cells control these barriers by regulating the movement of water, ions, and proteins across them. Flow of ions and molecules between cells, often referred to as the paracellular permeability pathway, is regulated by tight junctions. (Koval, Michael. Claudins —Key Pieces in the Tight Junction Puzzle. *Cell Communication and Adhesion*. 13:127-138, 2006.)

Tight junctions are sites of cell-cell contact composed of a number of transmembrane and peripheral proteins, assembled into a complex tethered to the cytoskeleton. Of these transmembrane proteins, those identified as "claudins" are the major determinant of cellular permeability. Claudins serve several roles in maintaining barrier function. Claudins are a major component of the strands that constitute the permeability barrier to limit diffusion of proteins and other macromolecules between cells, and they also form specific paracellular channels that regulate ion diffusion between cells. Claudin-1 mutations have been associated with several types of ichthyosis (a family of skin disorders causing dry, thickened, scaly, or flaky skin), and a study has shown that the epidermal barrier function of claudin-1 deficient mice is so compromised that their cells are unable to hold water, causing the skin to dry up and leading to death within a day. (M. Furuse, et al. *The Journal of Cell Biology*, 156 (No. 6): 1099-1111, 2002)

Aquaporin-3 (AQP3) is a membrane transporter of water and glycerol expressed in the basal layer of epidermal keratinocytes. Aged human skin has been shown to experience decreased AQP3 expression, which also correlates to a reduced stratum corneum water content and elasticity compared to young, undamaged skin. In studies involving AQP3-knockout mice, reduced AQP3-dependent glycerol transport in AQP3-deficient epidermis has been shown to be responsible for dehydrated, inelastic skin. ("Aquaporin-3 functions as a glycerol transporter in mammalian skin," Hara-Chikuma M, Biol Cell. 2005 July; 97(7):479-86.); ("Roles of Aquaporin-3 in the Epidermis", Hara-Chikuma, M., J Invest Dermatol. 2008 September; 128(9):2145-51. Epub 2008 Jun. 12); ("Glycerol replacement corrects defective skin hydration, elasticity, and barrier function in aqaporin-3-deficient mice," Hara M., Proc Natl Acad Sci USA. 2003 Jun. 10; 100(12):7360-5. Epub 2003 May 27).

The blend of banyan tree, clover, and lotus serum fractions resulted in positive increases in barrier function and moisture, as evidenced by the statistically significant up-regulation of claudin-1 and aquaporin-3 ("AQP3") in Example 3 below.

In Example 2, the blend's effect on three different genes associated with aging skin was evaluated. These three genes, and their associated functions, are described in Table 1 of Example 2. The fold-increase/decrease in expression, versus control, was determined for the aging-related genes at two different concentration levels. In both cases, as shown in Tables 2a and 2b, the blend effected a positive fold increase in all nine genes, indicating the desirable up-regulation of that gene, and thus a positive anti-aging benefit.

EXAMPLES

Example 1

Exemplary Compositions

Table 1 sets forth non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All examples may be used to treat or improve the appearance of one or more signs of aging. The present invention may further relate to a regimen involving the localized treatment for one or more aging signs by a first composition (e.g., Examples A or B) and a more broad or general facial skin treatment by a second composition (e.g., Examples C or D), which can be applied before or after the localized treatment to improve a particular sign of aging (e.g., across the entire face).

TABLE 1

Exemplary Compositions

| | % by wt. | | | |
|---|---|---|---|---|
| Component | Example A | Example B | Example C | Example D |
| *Ficus Benghalensis* (Banyan Tree) Flower/Leaf/Stem Juice (manufactured by Integrated Botanical Technologies) | 0.55 | 1.00 | 0.55 | 0.00 |
| *Nelumbo Nucifera* (Lotus) Flower/Leaf/Stem Juice (manufactured by Integrated Botanical Technologies) | 0.10 | 0.20 | 0.20 | 0.00 |
| *Trifolium Pratense* (Clover) Flower/Leaf/Stem Juice (manufactured by Integrated Botanical Technologies) | 0.10 | 0.20 | 0.20 | 0.00 |
| N-Acetylglucosamine | 0.00 | 0.00 | 2.00 | 0.00 |
| Hexamidine Diisethionate | 0.00 | 0.00 | 0.09 | 0.09 |
| Sepiwhite ™ (Undecylenoyl- | 0.00 | 0.00 | 0.50 | 0.50 |

TABLE 1-continued

Exemplary Compositions

| Component | % by wt. | | | |
|---|---|---|---|---|
| | Example A | Example B | Example C | Example D |
| phenylalanine, neutralized) (available from SEPPIC) | | | | |
| Sepigel 305 ™ (Polyacrylamide + C13-14 isoparaffin + laureth-7) (available from SEPPIC) | 0.00 | 0.00 | 2.00 | 2.00 |
| Dipotassium Glycyrrhizate | 0.00 | 0.10 | 0.10 | 0.30 |
| Hexamidine Diisethionate | 0.00 | 0.00 | 0.09 | 0.09 |
| Homosalate | 0.00 | 0.00 | 0.00 | 9.00 |
| Avobenzone | 0.00 | 0.00 | 0.00 | 3.00 |
| Octocrylene | 0.00 | 0.00 | 0.00 | 2.60 |
| Oxybenzone | 0.00 | 0.00 | 0.00 | 1.00 |
| Octisalate | 0.00 | 0.00 | 0.00 | 4.50 |
| Butylene Glycol (CAS No. 107-88-0) | 5.50 | 5.50 | 5.50 | 5.50 |
| Niacinamide (CAS No. 98-92-0) | 5.00 | 5.00 | 5.00 | 5.00 |
| Glycerin (CAS No. 56-81-5) | 2.50 | 2.50 | 2.50 | 2.50 |
| DC 1503 Fluid ™ (available from DowCorning) | 2.50 | 2.50 | 2.50 | 2.50 |
| Lubrajel Oil ™ (available from Sederma) | 1.44 | 1.44 | 1.44 | 1.44 |
| Phenonip XB ™ (available from Clariant) | 1.25 | 1.25 | 1.25 | 1.25 |
| D-panthenol (CAS No. 81-13-0) | 1.00 | 1.00 | 1.00 | 1.00 |
| Tospearl 2000 ™ (Polymethylsilsesquioxane) (CAS No. 68554-70-1) (available from GE Silicones/Momentive) | 1.00 | 1.00 | 1.00 | 1.00 |
| DL-Alpha Tocopheryl Acetate (CAS No. 7695-91-2) | 0.50 | 0.50 | 0.50 | 0.50 |
| Prodew 400 ™ (available from Ajinomoto) | 0.50 | 0.50 | 0.50 | 0.50 |
| Pemulen TR-2 ™ (Acrylates/C10-30 Alkyl Acrylate Crosspolymer) (available from Noveon) | 0.25 | 0.25 | 0.25 | 0.25 |
| Polysorbate 20 (CAS No. 9005-64-5) | 0.25 | 0.25 | 0.25 | 0.25 |
| Sodium Metabisulfite (CAS No. 7681-57-4) | 0.25 | 0.25 | 0.25 | 0.25 |
| Allantoin (CAS No. 97-59-6) | 0.20 | 0.20 | 0.20 | 0.20 |
| Sodium Hydroxide (CAS No. 1310-73-2) (50% solution by weight in water) | 0.17 | 0.17 | 0.17 | 0.17 |
| Disodium EDTA (CAS No. 139-33-3) | 0.10 | 0.10 | 0.10 | 0.10 |
| Xanthan Gum (CAS No. 11138-66-2) | 0.05 | 0.05 | 0.05 | 0.05 |
| Sodium Hyaluronate (CAS No. 9067-32-7) | 0.01 | 0.01 | 0.01 | 0.01 |
| Water (CAS No. 7732-18-5) | QS | QS | QS | QS |
| TOTAL (% by weight of total composition) | 100.00 | 100.00 | 100.00 | 100.00 |

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (e.g., physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Example 2

Ex Vivo Tissue Analysis

Individual banyan tree, lotus, and clover serum fractions, as well as their blend, were evaluated at two different concentrations according to the method described herein. The fold-increase/decrease in expression, versus control, was determined for the aging-related genes set forth in Table 1, below. A positive fold increase indicates the desirable up-regulation of that gene, and thus a positive anti-aging benefit.

Ex Vivo tissue Method: Skin explants were collected from surgical waste and treated with actives in media. Control skin was untreated. After 7 days, punch biopsies were taken for RNA isolation and PCR analysis.

RT-PCR Method: Purified RNA is converted to cDNA using Quanta iScript™. 500 ng of RNA is mixed with iScript and run on a thermocycler according to kit instructions. One ul of the resulting cDNA is then mixed with Quanta Perfecta Master™ mix according to instructions and aliquoted across SAbiosciences™ custom array plate. The plate is then sealed and run on the Step-one Plus™ machine from Applied Biosystems™. The data analysis is performed by uploading raw data into the data analysis software from SAbiosciences™.

TABLE 1

Representative Genes Having Decreased Expression with Skin Aging

| Gene | Associated Function |
|---|---|
| Fibrillin-1 (FBN1) | Structural components of microfibrils, which occur in association with elastin |
| Fibronectin-1 (FN1) | Adhesive associated with wound healing |
| Collagen 3, a1 (COL3A1) | Major collagen of the dermis |

TABLE 2a

Sample Concentration 1
Up-Down Regulation
Fold Change vs. Control

| Gene | Clover Serum Fraction 0.1% | Banyan Tree Serum Fraction 0.55% | Lotus Serum Fraction 0.1% | Combination (statistically significant vs. control p ≦ 0.05) |
|---|---|---|---|---|
| FBN1 | 1.11 | 1.46 | 2.24 | 3.85 |
| FN1 | −1.07 | 1.07 | −1.06 | 1.37 |
| COL3A1 | −1.21 | 1.32 | −1.12 | 1.69 |

TABLE 2b

Sample Concentration 2
Up-Down Regulation
Fold Change vs. Control

| Gene | Clover Serum Fraction 0.01% | Banyan Tree Serum Fraction 0.05% | Lotus 0.01% | Combination (statistically significant vs. control p ≦ 0.05) |
|---|---|---|---|---|
| FBN1 | 1.23 | 1.07 | 1.48 | 3.20 |
| FN1 | 1.18 | −1.15 | −1.05 | 1.56 |
| COL3A1 | 1.10 | −1.13 | 1.08 | 2.07 |

Example 3

Keratinocyte Assay for Claudin 1 and AQP-3 Expression

Keratinocyte Culture: A multiplex mRNA analysis was conducted. RNA was isolated from neonatal human keratinocytes. Neonatal human keratinocytes (Cascade Biologics #C-001-5C) were grown to 40% confluence in 6-well tissue culture plates then treated with compounds for 24 hours (3 replicates per treatment). The treatments included several concentrations of banyan tree +clover +lotus blends along with individual juices. Additionally, a vehicle control was used.

Several targets were measured with Panomics QuantiGene Plex Assay kit, a multi-analyte quantitative bead-based assay. The fluorescence intensity values, measured by a Bio-Rad Bio-Plex 100 instrument, for those samples yielding sufficient RNA are shown for AQP-3 and claudin-1.

The graph of FIG. 1 shows that claudin-1 and AQP3 were desirably up-regulated in response to the banyan tree+clover+lotus blend herein.

Example 4

Method of Treatment

A test subject topically applies a composition comprising 0.55% ficus serum fraction+0.1% clover serum fraction+0.1% lotus serum fraction, by weight in a vehicle, to the entire face one to two times a day for 8 weeks. Transepidermal Water Loss (TEWL) and Corneometer data is collected at time 0, 4 hours, 1, 2, 3, 4, and 8 weeks. TEWL and Corneometer data show an immediate (acute benefit) improvement in skin hydration at 4 hours, as well as sustained improvement (chronic benefit) in skin hydration measured over the successive weeks. In addition, even after the subject stops using the test composition, the skin maintains improved hydration over several weeks. During and several weeks after treatment, the subject's facial skin feels and appears to be more hydrated, and the subject notices a decrease in the appearance of fine lines and wrinkles The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of aging skin comprising the step of applying a first composition comprising:
   a. an effective amount of banyan tree serum fraction, lotus serum fraction, and clover serum fraction blend; and
   b. a dermatologically acceptable carrier;
   to a skin surface having at least one sign of aging, wherein the composition is applied for a period of time sufficient to improve the appearance of the at least one sign of aging.

2. The method of claim 1, wherein the first composition comprises, by weight of the total composition:
   a. from 0.001% to 15% banyan tree serum fraction;
   b. from 0.001% to 15% lotus serum fraction; and
   c. from 0.001% to 15% clover serum fraction.

3. The method of claim 1 wherein the skin surface is a facial skin surface.

4. The method of claim 3, wherein the first composition is applied to at least one of a forehead, perioral, chin, periorbital, nose, and cheek skin surfaces.

5. The method of claim 4, wherein the first composition is applied to each of the forehead, periorbital, perioral and cheek skin surfaces.

6. The method of claim 1, wherein the first composition is applied at least once a day for at least about four weeks.

7. The method of claim 1, wherein the first composition is applied at least twice a day for at least about four weeks.

8. The method of claim 1, wherein the first composition is applied at least once a day for at least about eight weeks.

9. The method of claim 1, wherein the first composition is applied at least twice a day for at least about eight weeks.

10. The method of claim 1, wherein the first composition further comprises a sunscreen active.

11. The method of claim 1, wherein the first composition further comprises an anti-inflammatory agent.

12. The method of claim 11, wherein the anti-inflammatory agent is selected from glycyrrhizic acid, glycyrrhizic acid salts, licorice extract, bisabolol, and combinations thereof.

13. The method of claim 1, wherein the first composition further comprises a skin tone agent.

14. The method of claim 13, wherein the skin tone agent is selected from the group consisting of vitamin B3 compounds, sugar amines, hexamidine compounds, salicylic acid, 1,3-dihydroxy-4-alkylbenzene, retinoids, and combinations thereof.

15. The method of claim 1, wherein the first composition is applied to a plurality of signs of skin aging for a period of time sufficient to improve the appearance of the plurality of signs of skin aging.

16. The method of claim 1, further comprising a step of applying a second composition to the skin surface.

17. The method of claim 1, wherein the second composition comprises an effective amount of banyan tree serum fraction, lotus serum fraction, and clover serum fraction.

18. The method of claim 16, wherein the second composition comprises a sunscreen active, an anti-inflammatory agent, or a skin tone agent.

19. The method of claim 18, wherein a skin tone agent is selected from the group consisting of vitamin B3 compounds, sugar amines, hexamidine compounds, salicylic acid, 1,3-dihydroxy-4-alkylbenzene, retinoids, and combinations thereof.

20. A composition for improving the appearance of aging skin, comprising:
   a. an effective amount of banyan tree serum fraction, lotus serum fraction, and clover serum fraction; and
   b. a dermatologically acceptable carrier.

* * * * *